(12) United States Patent
Augier et al.

(10) Patent No.: US 8,318,024 B2
(45) Date of Patent: Nov. 27, 2012

(54) SYSTEM AND METHOD FOR DISTRIBUTION OF FLUID A MULTISTAGE COLUMN

(75) Inventors: Frederic Augier, Saint Symphorien D Ozon (FR); Denis Darmancier, Vienne (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 535 days.

(21) Appl. No.: 12/492,476

(22) Filed: Jun. 26, 2009

(65) Prior Publication Data

US 2010/0101999 A1  Apr. 29, 2010

(30) Foreign Application Priority Data

Jun. 27, 2008 (FR) ...................................... 08 03693

(51) Int. Cl.
*B01D 15/18* (2006.01)
(52) U.S. Cl. ......... 210/690; 210/264; 210/284; 210/289
(58) Field of Classification Search ............... 210/198.2, 210/264, 289, 283–285, 291, 456, 269, 656, 210/672

See application file for complete search history.

(56) References Cited

U.S. PATENT DOCUMENTS

| | | | | |
|---|---|---|---|---|
| 3,523,762 | A | * | 8/1970 | Broughton .................... 422/638 |
| 3,789,989 | A | * | 2/1974 | Carson .......................... 210/284 |
| 5,755,960 | A | | 5/1998 | Callebert et al. |
| 6,471,861 | B1 | | 10/2002 | Burgard et al. |
| 7,051,758 | B2 | * | 5/2006 | Bellqvist et al. .......... 137/561 A |
| 2003/0127394 | A1 | | 7/2003 | Hotier |
| 2006/0108274 | A1 | | 5/2006 | Frey et al. |
| 2008/0041780 | A1 | | 2/2008 | Frey et al. |

FOREIGN PATENT DOCUMENTS

| | | |
|---|---|---|
| EP | 0 769 316 A1 | 4/1997 |
| EP | 1 325 772 A1 | 7/2003 |
| FR | 2 740 054 A1 | 4/1997 |
| WO | WO 2006/055222 A1 | 5/2006 |

OTHER PUBLICATIONS

International Search Report of 08/03.693 (Jan. 22, 2009).

* cited by examiner

*Primary Examiner* — Matthew Savage
(74) *Attorney, Agent, or Firm* — Millen, White, Zelano & Branigan, P.C.

(57) ABSTRACT

The present invention consists of a device for distributing and collecting fluids at the outlet from an upstream granular bed in a multistage column having a plurality of granular beds, said device comprising a deflector, which can equalize the trajectories of the fluid stream lines from the outlet from the mixing chamber to the downstream bed of granular solid.

14 Claims, 4 Drawing Sheets

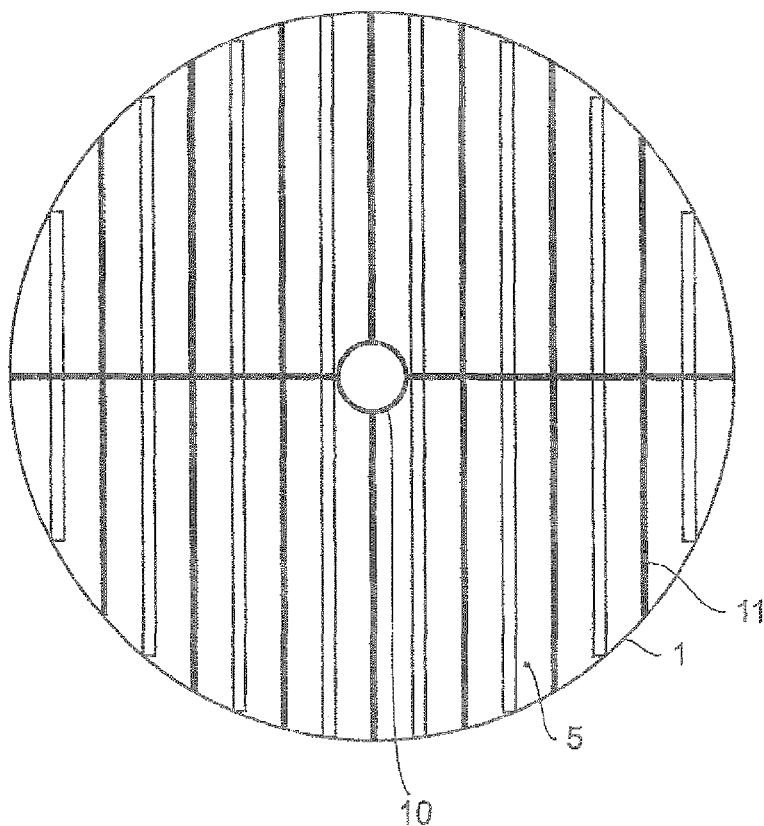
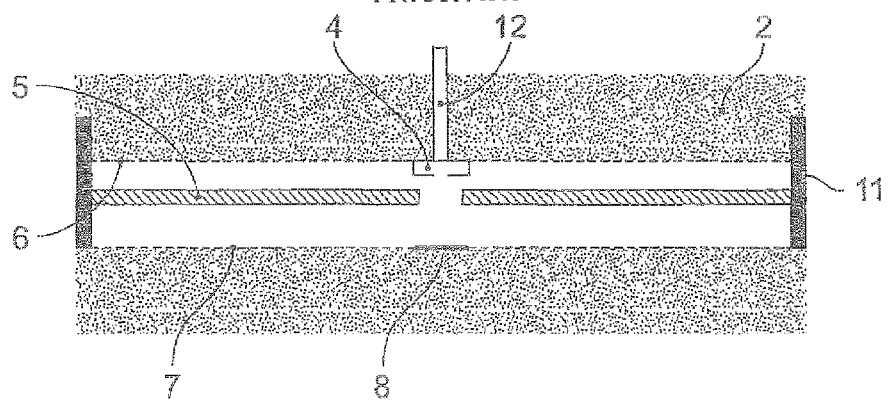

SYSTEM AND METHOD FOR DISTRIBUTION OF FLUID A MULTISTAGE COLUMN

CROSS-REFERENCE TO RELATED APPLICATION

This application is related to a concurrently filed application Ser. No. 12/493,684 entitled "NOVEL FLUID DISTRIBUTION AND COLLECTION SYSTEM IN A MULTISTAGE COLUMN COMPRISING A JET BREAKER", Frederic Augier, claiming priority of French application 08/03.692 filed Jun. 27, 2008.

FIELD OF THE INVENTION

The invention relates to a novel device for distributing and collecting fluids in a multistage column employing a flow of said fluids in a solid particle medium termed a granular medium.

The term "multistage column" is applied to a column constituted by a plurality of plates disposed along a substantially vertical axis, each plate (termed the support plate) supporting a bed of granular solid, and the various successive beds being traversed in series by the fluid or fluids employed in the column. The fluid traversing the successive beds is termed the principal fluid in order to distinguish it from other fluids, termed secondary fluids, which may be added to the principal fluid via plates generally located between two successive beds and termed distributor plates.

Each bed is generally supplied via a distributor plate located upstream of said bed. In the remainder of the text, when the abbreviated term "plates" is used, this means the distributor plate.

A distributor plate typically comprises a network for supplying or collecting fluids, termed a distribution network, and one or more mixing chambers intended to mix the fluid injected or withdrawn via the distribution network with the principal fluid.

EXAMINATION OF THE PRIOR ART

In multistage processes of the reactor or separation column type, the distribution devices employed may have several functions such as injection or withdrawal of a flow of fluid in the reactor or column at any level of said column. It is generally desirable for this function of injection or withdrawal to be carried out in a manner which is equilibrated between the various regions of the column section.

The section of the column is generally divided into a certain number of sectors or panels, each sector having to be irrigated in a homogeneous manner with respect to the others.

This requires the use of distributors with a particular geometry, which can reach each sector and deliver (or remove) an approximately equal flow to each of the sectors, if the surface areas are equal. If the surface areas are different, the flows which are injected or removed are approximately proportional to the surface area of the associated sectors.

The plates also fulfill the function of mixing between the principal flow in the column and the secondary stream or streams injected by the network, in order to supply the downstream plates with a fluid with a homogeneous concentration. The following patents: WO-2006/027118A1, US-2006/0108274A1, EP-0 074 815, FR-93/09593, provide examples of the configurations of distributor plates in processes for separation by adsorption in multistage columns of the chromatographic or simulated moving bed type (SMB).

The distribution network associated with a plate supplies said plate via a limited number of injection points. Depending on the manner in which the plate is divided into panels, one injection point per panel is generally used, but two or three points per panel are also entirely suitable.

The panels are generally designed so as to encourage mixing between the principal flow from the upper bed and the secondary flow injected via the distribution network. To this end, the panels are open over a small fraction of their surface, such that the principal flow flows close to the injection point for the network into the panel. Thus, the two flows, principal and secondary, are mixed before being re-distributed over the entire (or almost the entire) of the surface of the panels.

Collection of the flows leaving the bed upstream of the plate then re-distribution of that flow over the section of the plate is an operation which must generate the minimum axial dispersion in order to keep the flow as close to plug flow as possible. This is particularly important with simulated moving bed (SMB) separation processes. The axial dispersion induced by the plates is largely due to the distribution of the residence time in the collection and re-distribution zones. The residence time of a line of fluid in the plate in fact depends principally on the inlet and outlet positions of said line at the plate, as will be explained below.

In contrast to stationary fixed bed flows, where plug flow is desired across the granular bed without being concerned with the nature of the flow in the distribution device at the inlet or collection point at the bed outlet, in the flows envisaged in the present invention, it is essential to have plug flow both in the granular medium and across the distribution and collection devices. In a SMB adsorption process, the species are separated by passage through a bed of particles (or adsorbant) but any deviation from plug flow outside the bed tends to re-mix the species and thus the separation performance deteriorates.

One way of limiting the dispersion induced by the plates is to use a large number of divisions into sectors or panels, the consequence being a large number of network supplying points at the plates. This means that the distances which are to be covered by the fluid can be minimized from the panel openings to the various regions of the solid particle bed, and this means that the dispersion induced by the plates can be minimized. This solution generates an increase in plate manufacturing costs.

BRIEF DESCRIPTION OF THE FIGURES

FIG. 1A, in accordance with the prior art, is a representation of the division of the plates into meridional panels;

FIG. 1B, in accordance with the prior art, is a diagrammatic representation of a meridional panel of a distributor plate;

BRIEF DESCRIPTION OF THE INVENTION

Figure 2A:
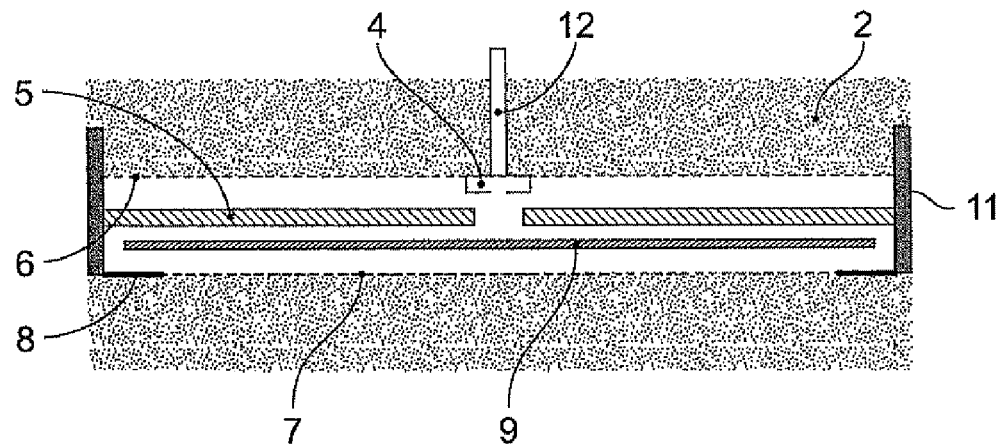
FIG. 2A, in accordance with the invention, represents a section of a meridional panel provided with a deflector placed below the collection baffle.

The problem to be overcome by the present invention is that of improving the flow of fluids inside a column comprising a plurality of plates each carrying a bed of granular solid, termed a multistage column.

The term "improving the flow" as used in the present context means that the flow is as close to plug flow as possible, i.e. a flow in which the axial dispersion of fluid passing through the various successive beds of the column is as small as possible, including passage through the devices for distribution and collection of said fluid or fluids.

The aim of the present invention is to minimize the dispersion generated by the distributor plates by optimizing the disposition of the collection and injection zones of the beds. The invention pertains to the use of distributor plates so that the positions of the supply and collection zones belonging to each bed can be staggered in order to minimize the residence time distribution between two distributor plates. Two embodiments of the invention have been developed:

By equipping the panels composing the plates of a deflector disposed in a suitable manner, the residence time distribution in the plates has an axial dispersion which is substantially reduced. The effect of a properly positioned deflector is to provide an overall equilibration of the residence time distribution for the various lines of fluid in the supply zone at the inlet to the bed and in the collection zone at the bed outlet.

Thus, the various lines of fluid passing through a granular bed from the inlet panel to the outlet panel inclusive will have substantially identical residence times.

The distributor plates are generally divided into independent panels functioning in parallel, each panel processing a fraction of the "principal" flow arriving from the bed above.

The present invention is applicable to all or part of the panels dividing the section of the column. The invention is also applicable to an undivided plate provided that this case is equivalent to that of a single panel itself constituting the plate.

The panels generally comprise a plate or collection baffle which is partially open acting to collect the principal flow leaving the bed above in order to facilitate mixing with a secondary flow injected into the panel.

The invention aims to stagger the zones for collecting flows entering a bed and the zones for collecting flows leaving the same bed of granular solid. The invention is carried out by integrating into the panels an element termed a solid deflector which can route the principal flow, before or after its passage through the collection baffle, in zones which are laterally distanced from the baffle opening. The term "solid" means that the deflector is not porous and thus forces the entire flow to go round it.

More precisely, the invention consists of a device for distributing a fluid supplying at least one granular bed of a multistage column having a succession of plates, each plate P supporting a bed of granular solid and being divided into adjacent panels, denoted Pa, covering the whole of the column section, said device being applied to at least a portion of the panels Pa of the plate P, said device comprising:

a) a screen or perforated plate termed the upper screen 6 acting to support the bed of particles 2 located above the plate;

b) a collection baffle 5 which is open at its centre;

c) a distributor 7 composed of a screen or a perforated plate for re-distributing the flow leaving the panel over the entire surface of the bed of particles located below the panel;

d) a solid deflector 9 placed between the collection baffle 5 and the distributor 7, in a position denoted P1, or placed between the upper screen 6 and the collection baffle 5, in a position denoted P2.

In a variation of the device of the invention, said device additionally comprises a jet breaker 8 positioned above or below the distributor 7, and placed at the edges of the panel Pa when the deflector 9 is in position P1 or placed substantially in line with the opening of the collection baffle 5 when the deflector 9 is in position P2.

The device of the invention is applicable to panels Pa of the meridional type, i.e. rectangular, orientated in the same direction in length, and having substantially the same width.

The device of the invention is also applicable to panels Pa having the shape of radial sectors, each sector having substantially the same angle of opening.

The invention may also be described as a process for simulated moving bed separation using a device of the invention, in which the feed to be separated is any mixture of aromatic compounds containing 7 to 9 carbon atoms.

The invention may also be envisaged as a process for simulated moving bed separation using a device of the invention, in which the feed to be separated is a mixture of normal and iso-paraffins.

The invention may also be envisaged as a process for simulated moving bed separation using a device of the invention, in which the feed to be separated is a mixture of normal and iso-olefins.

The invention may also be viewed as a process for simulated moving bed separation using a device of the invention, in which the principal fluid passing through said device has a density in the range 600 to 950 kg/m$^3$ and a viscosity in the range 0.1 to 0.6 cPo.

DETAILED DESCRIPTION OF THE INVENTION

FIG. 1A represents a column section 1 divided into a multitude of panels 11 which are approximately rectangular in shape, adjacent to each other and orientated in the same direction corresponding to the length. The dimension perpendicular to the length of a panel in the plane corresponding to a column section is termed the width of the panel. In general, the set of meridional panels covering a column section has a common width and different lengths. This type of panel will hereinafter be termed the meridional panel. The column is equipped with a central support 10 bearing support beams which are perpendicular to the axis of the support. The panels are composed of a frame defining them, and by a collection baffle 5 which is open along a strip located approximately at the centre of said panel in the longitudinal dimension of said panel, and extending over its entire length.

FIG. 1B is a section of a prior art median panel. The meridional panel comprises a screen or perforated plate termed the upper screen 6 acting to support the bed of particles 2 located above the plate while allowing the passage of the principal flow leaving the bed. The panel also comprises a collection baffle 5 which is open at its centre, and a distributor 7 composed of a screen or a perforated plate which can re-distribute the flow leaving the panel over the entire surface of the bed of particles located below the panel.

The distributor 7 is often provided with a jet breaker plate 8 intended to prevent a jet of fluid from penetrating into the zone of the bed located below the opening of the collecting baffle 5. The panel also comprises a distribution system for injecting or collecting a secondary flow in the panel. The distribution panel is composed of a network of lines 12 which route the secondary flow and an injection chamber 4 located close to the opening of the collection baffle 5. The injection chamber 4 is positioned to allow proper mixing with the principal flow in the panel before re-distribution into the lower bed.

In this type of panel, any line of fluid leaving the upper bed passes through the collection baffle 5 after a certain time, this time depending on the position of the outlet for the line of fluid with respect to the baffle opening. The line of fluid leaving the bed just above the opening of the collection baffle 5 reaches the opening of said baffle sooner than the line of fluid coming from the edge of the panel. Similarly, the line of fluid entering the lower bed under the opening of the collection baffle 5 spends less time in the panel than the line of fluid entering the lower bed via the edge of the panel. The term "panel edge" is with respect to the width of said panel. Thus, the residence time in the panel varies fairly substantially depending on the stream lines followed by the fluid in the panel (which for simplification we have termed a line of fluid).

Figure 3A:
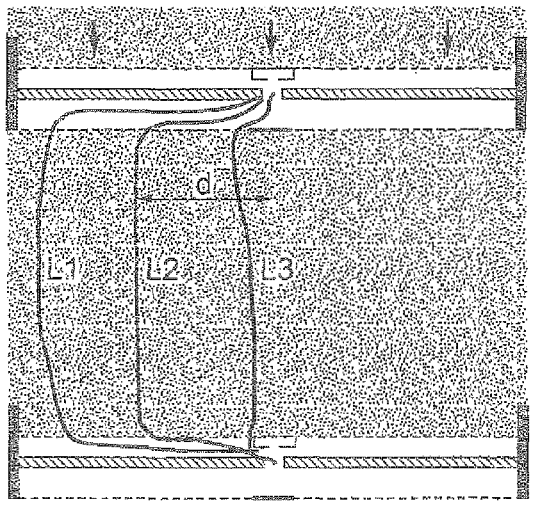
FIG. 3A shows the flow of fluid in a bed of particles when prior art panels are used.

This phenomenon produces an axial dispersion in the column which may be deleterious to the performances of the device. Examples of the various lines of fluid and the corresponding residence times are illustrated in FIGS. 3A and 3B which correspond to the prior art.

Figure 2B:
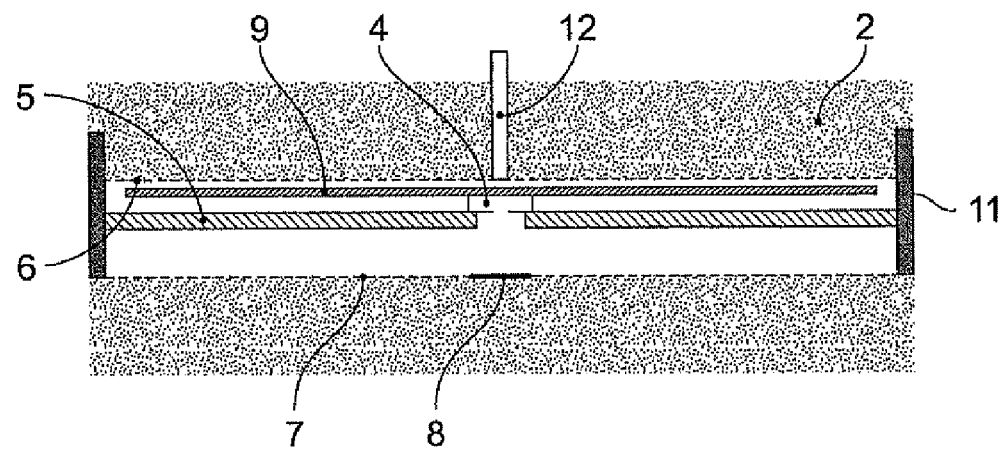
FIG. 2B, in accordance with the invention, represents a section of a meridional panel provided with a deflector placed above the collection baffle.

FIGS. 2A and 2B show a section of a meridional panel of the invention. The panels are identical to those shown in prior art FIG. 1B, except that they include a novel element termed a deflector 9 which may be positioned above or below the collection baffle 5.

In FIG. 2A, the deflector 9 is positioned below the collection baffle 5 (the position is denoted P1) so that the fluid leaving the baffle is routed into the zones of the panel which are furthest from the centre, i.e. furthest from the opening of said baffle. Thus, the fluid leaving the panel enters the lower bed via the off-centre zones of the panel and is then distributed over the entire surface of the bed. As shown in FIG. 2A, the deflector (9) has a thickness and a pair of parallel edges. The deflector is positioned adjacently between and spaced apart from the collection baffle (5) and the distributor (7) with each parallel edge being adjacently spaced apart from a respective one of the parallel walls of the panel. The distance between each parallel edge of the deflector (9) and the adjacent parallel wall of the panel (Pa) of the plate (P) is in the range of 5 to 200 mm and the thickness of the deflector (9) is in the range of 0.5 to 10 mm. The jet breaker plates 8 are positioned over and on the distributor in the high velocity zones, i.e. close to the ends of the deflector 9 and placed at each of the parrallel walls of the panel.

FIG. 2B corresponds to the case in which the deflector 9 is positioned above the collection baffle 5 (the position termed P2). In this case, the baffle 9 routes the fluid towards the end of the panel width. The fluid is then collected by the collection baffle 5 then re-distributed from the centre over the section of the panel.

FIG. 3A represents a bed of solid particles included between two panels which are aligned in accordance with the prior art. The term "aligned panels" means two successive panels in the direction of fluid flow are located face to face.

FIG. 3A shows 3 lines of fluid L1, L2 and L3. The lines of fluid are the paths followed by the various fluid elements leaving the collection baffle 5 of the panel above. The lines of fluid are approximately parallel through the bed of particles due to the high pressure drop in the bed.

The fluid entering the bed at a certain distance d from the centre of the panel leaves the bed at approximately the same distance d from the centre of the next panel.

As a consequence, the various lines of fluid have residence times T between the two successive collection baffles which differ significantly, as shown in FIG. 3B. As an example, the fluid following the stream line L1 has a residence time T which is longer than the fluid following the stream line L3, since the fluid which follows line L1 spends a non negligible time in the upstream collection and re-distribution zones.

Figure 3C:
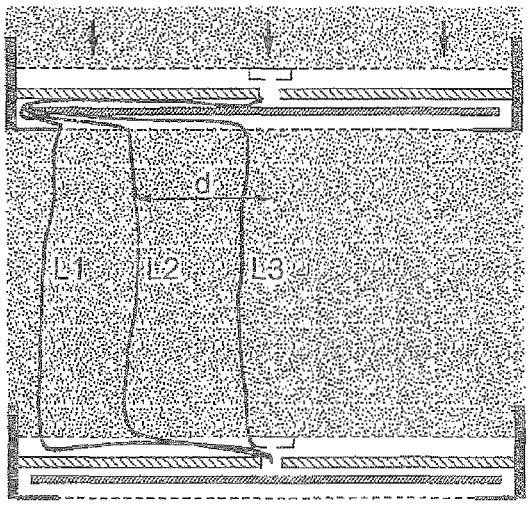
FIG. 3C illustrates the flow of fluid in a bed of particles when the panels of the invention are used.
Figure 3B:
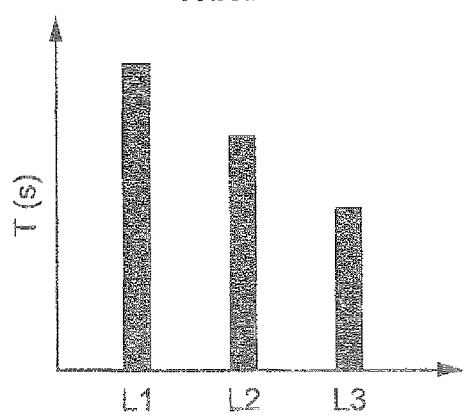
FIG. 3B is a diagrammatic representation of the residence time associated with various stream lines in a bed of particles when prior art panels are used.
Figure 3D:
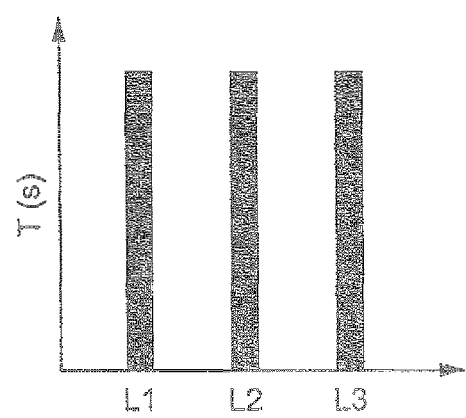
FIG. 3D is a representation of the residence times associated with various stream lines in a bed of particles when the panels of the invention are used.

FIG. 3C gives a representation of a bed of solid particles included between two aligned panels in accordance with the invention. The deflector 9 is in this case positioned below the collection baffle. Because of the presence of the deflector 9, the lines of fluid are routed at the edge of the panel before being distributed over the section of the bed. The lines of fluid L1, L2 and L3 now have similar residence times T, as shown in FIG. 3D.

Regardless of the distance d of the fluid entry point with respect to the centre of the panel, the overall residence time of a line of fluid between two successive collection baffles is approximately identical.

The deflector 9 thus has the effect of equalizing the residence time for the various lines of fluid, regardless of their distance d of entry into the granular bed.

Figure 4A:
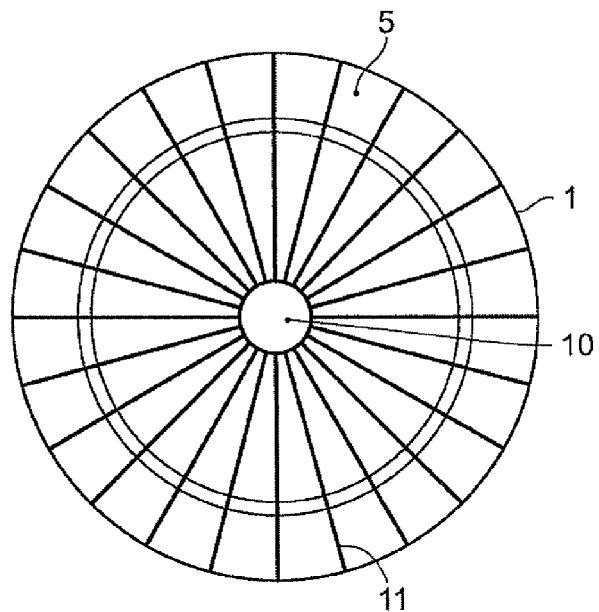
FIG. 4A, in accordance with the prior art, represents division of a plate into radial sectors.

FIG. 4A is a diagrammatic representation of a plate divided into identical radial sectors.

Figure 4B:
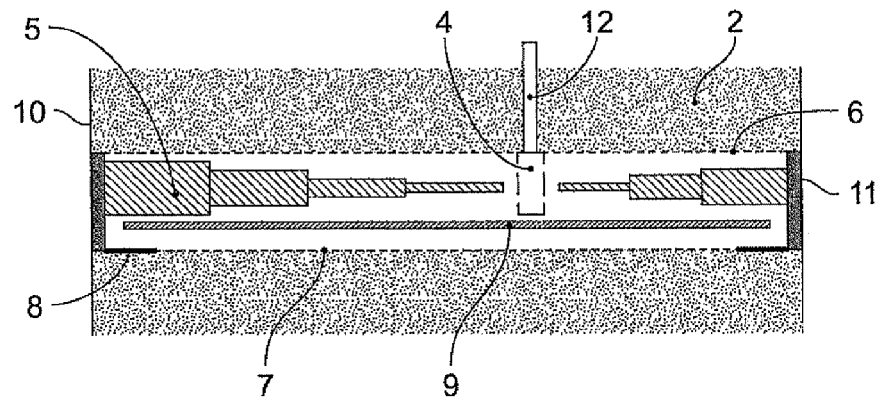
FIG. 4B, in accordance with the invention, represents a section of a radial sector provided with a deflector in accordance with the invention.

FIG. 4B represents a radial sector 11 of the invention. The collection baffle 5 is generally composed of steps with different thicknesses, although this is not obligatory. The deflector 9 is placed below the collection baffle 5. In a variation of the invention, this deflector 9 may be placed above said collection baffle 5.

The elements denoted 2, 4, 12, 8 and 7 have the same meaning and function as the elements with the same number already described in the case of FIG. 1B.

Figure 4C:
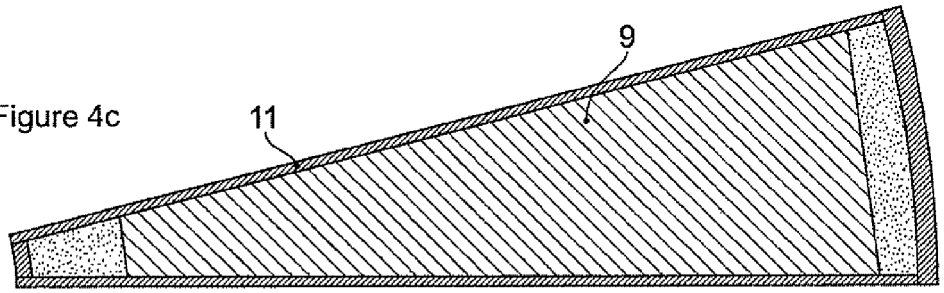
FIG. 4C is a top view of a radial sector, showing the deflector and the frame of the panel.

FIG. 4C is a top view of a panel 11 in the form of a sector, where only the frame of the panel and the deflector 9 are shown.

The deflector positioned above or below the collection baffle may be produced using any solid plate with a width strictly less than that the width of a panel, and with a length substantially equal to that of the panel, such that the free space located between the end of the deflector and the edge of the panel has a surface area close to half that of the opening in the baffle 5. Thus, the velocity at which the liquid passes either side of the deflector will be close to the velocity of the liquid passing through the baffle 5 since the liquid flow will pass into the nearby open surfaces. The distance between the end of the deflector and the edge of the panel is in the range 5 to 200 mm, preferably in the range 10 to 50 mm. The thickness of the deflector is in the range 0.5 to 10 mm, preferably in the range 1 to 3 mm.

EXAMPLE

The invention's efficacy was tested using mock-up tests. The mock-up reproduced a bed of solid particles included between two prior art panels on the one hand and of the invention on the other hand, as can be seen in FIGS. 3A and 3C.

The mock-up reproduced the geometry between the two collection baffles. The width of the meridional panel was 1.2 m; the bed height was 1.2 m. The depth of the mock-up was 18 cm. The collection baffle was perforated with holes 30 mm in diameter with a centre-to-centre separation of 60 mm. The distance between the upper screen and the collection baffle was 10 mm. The distance between the collection baffle and the distributor was 20 mm.

The deflector used was 1 mm thick and was positioned 5 mm below the collection baffle.

The deflector was 1.1 m wide and thus was open 5 cm from each side of the panel.

The mock-up was filled with 1 mm diameter glass beads to a height of 10 mm below the distributor.

The mock-up was supplied with water at a superficial velocity equivalent to 1.5 cm/s.

For each configuration (with/without deflector), the hydrodynamics were characterized by measuring the residence time distribution (RTD).

The RTD method has been explained in many works, including "Génie de la reaction chimique" [Engineering chemical reactions] by D Schweich, 2001, pub. Tec&Doc, Paris. The results are shown in the form of the Peclet number (Pe) which expresses the ratio between the flow velocities by convection and by diffusion. The higher the Peclet number (Pe), the smaller the axial dispersion between the two collection baffles, and thus the closer the flow approaches plug flow (i.e. without axial mixing of the flowing fluid sections). The results are shown in Table 1.

TABLE 1

Comparison of hydrodynamics with or without deflector. These results show that the invention can very significantly improve the hydrodynamics in multistage columns (increase of +75% in the Peclet number).

| Configuration | Peclet |
|---|---|
| No deflector | 200 |
| With deflector | 350 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 08/03.693, filed Jun. 27, 2008 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A fluid distribution device suitable for use within a multistage column containing a plurality of granular beds, said fluid distribution device comprising:
a plate (P) divided into meridional adjacent panels, denoted (Pa), by parallel walls, each of said panels having a shape that is approximately rectangular and all of said panels having sides of a longest dimension oriented along the same direction in length that is parallel to the parallel walls of said plate, wherein at least one of said panels (Pa) comprises:
a) an upper screen or upper perforated plate (6) suitable for supporting a bed of granular particles (2) above said at least one panel (Pa) of said plate (P);
b) a distributor (7) comprising a screen or a perforated plate suitable for re-distributing fluid flowing through said at least one panel (Pa) of said plate (P);
c) a collection baffle (5) having a substantially central opening positioned between said upper screen or upper perforated plate (6) and said distributor (7);
d) a deflector (9) having a thickness and a pair of parallel edges, said deflector being positioned adjacently between and spaced apart from said collection baffle (5) and said distributor (7), each said parallel edge being adjacently spaced apart from a respective one of the parallel walls of the panel, wherein the distance between each said parallel edge of said deflector (9) and the adjacent said parallel wall of said at least one panel (Pa) of said plate (P) is in the range of 5 to 200 mm, and said thickness of said deflector (9) is in the range of 0.5 to 10 mm; and
e) a jet breaker plate (8) positioned on said distributor (7) and placed at each of said parallel walls of said at least one panel (Pa).

2. A fluid distribution device according to claim 1, wherein said deflector (9) has a length substantially equal to the length of said at least one panel (Pa) of said plate (P).

3. A fluid distribution device according to claim 1, wherein said adjacent panels (Pa) have substantially the same width.

4. A fluid distribution device according to claim 3, wherein said thickness of said deflector (9) is in the range of 1 to 3 mm.

5. A process for simulated moving bed separation comprising providing a device according to claim 1, and separating therein a feed of a mixture of aromatic compounds containing 7 to 9 carbon atoms, by conducting a simulated moving bed with said device.

6. A process for simulated moving bed separation according to claim 5, in which the feed to be separated is a mixture of normal and iso-paraffins.

7. A process for simulated moving bed separation according to claim 5, in which principal fluid passing through said device has a density in the range 600 to 950 kg/m$^3$ and a viscosity in the range 0.1 to 0.6 cPo.

8. A fluid distribution device according to claim 1, wherein said distance between the peripheral edge of said deflector (9) and said walls of said at least one panel (Pa) said distance is in the range of 10 to 50 mm.

9. A fluid distribution device according to claim 8, wherein said thickness of said deflector (9) is in the range of 1 to 3 mm.

10. A fluid distribution device according to claim 1, further comprising a line (12) suitable for injecting or collecting a fluid flow into or from said at least one panel (Pa) of said plate (P).

11. A fluid distribution device according to claim 10, further comprising an injection chamber (4) connected to said line (12) and located proximate to said substantially central opening of said collection baffle (5).

12. A fluid distribution device according to claim 1, wherein a plurality of said panels (Pa) comprise:
a) an upper screen or upper perforated plate (6) suitable for supporting a bed of granular particles (2) above said at least one panel (Pa) of said plate (P);

b) a distributor (7) comprising a screen or a perforated plate suitable for re-distributing fluid flowing through said at least one panel (Pa) of said plate (P);

c) a collection baffle (5) having a substantially central opening positioned between said upper screen or upper perforated plate (6) and said distributor (7) of each of the panels (Pa);

d) a deflector (9) having a thickness and a pair of parallel edges, said deflector being positioned adjacently between and spaced apart from said collection baffle (5) and said distributor (7), each said parallel edge being adjacently spaced apart from a respective one of the parallel walls of the panel, wherein the distance between each said parallel edge of said deflector (9) and the adjacent said parallel wall of said at least one panel (Pa) of said plate (P) is in the range of 5 to 200 mm, and said thickness of said deflector (9) is in the range of 0.5 to 10 mm; and e) a jet breaker plate (8) positioned on said distributor (7) and placed at each of said parallel walls of said at least one panel (Pa).

13. A multistage column comprising:

a plurality of beds of granular solid particles, each of said beds being supported by a plate (P), each of said plates (P) supporting one of the beds of granular solid particles, at least one of said plates (P) being divided into meridional adjacent panels, denoted (Pa), by parallel walls, each of said panels (Pa) having a shape that is approximately rectangular and all of said panels having sides of a longest dimension oriented along the same direction in length that is parallel to the parallel walls of said plate, and said panels (Pa) covering substantially the whole cross section of said column, wherein at least one of said panels (Pa) comprises:

an upper screen or upper perforated plate (6) suitable for supporting a bed of granular particles (2) located above said at least one panel (Pa) of said at least one plate (P);

a distributor (7) comprising a screen or a perforated plate suitable for re-distributing fluid flowing through said at least one panel (Pa) of said plate (P);

a collection baffle (5) having a substantially central opening positioned between said upper screen or upper perforated plate (6) and said distributor (7);

a deflector (9) having a thickness and a pair of parallel edges, said deflector being positioned adjacently between and spaced apart from said collection baffle (5) and said distributor (7), each said parallel edge being adjacently spaced apart from a respective one of the parallel walls of the panel, wherein the distance between each said parallel edge of said deflector (9) and the adjacent said parallel wall of said at least one panel (Pa) of said plate (P) is in the range of 5 to 200 mm, and said thickness of said deflector (9) is in the range of 0.5 to 10 mm; and a jet breaker plate (8) positioned on said distributor (7) and placed at each of said parallel walls of said at least one panel (Pa).

14. A process for simulated moving bed separation comprising providing a multistage column according to claim 13, and separating therein a feed of a mixture of aromatic compounds containing 7 to 9 carbon atoms, by conducting a simulated moving bed within said multistage column.

* * * * *